United States Patent [19]

Murakami

[11] Patent Number: 4,525,074

[45] Date of Patent: Jun. 25, 1985

[54] APPARATUS FOR MEASURING THE QUANTITY OF PHYSICAL EXERCISE

[75] Inventor: Tomomi Murakami, Higashimurayama, Japan

[73] Assignee: Citizen Watch Co., Ltd., Tokyo, Japan

[21] Appl. No.: 640,562

[22] Filed: Aug. 14, 1984

[51] Int. Cl.³ ............................................. G04B 47/00
[52] U.S. Cl. .................................. 368/10; 340/309.15
[58] Field of Search ....................... 368/10, 11, 82–84, 368/239–242; 340/526, 513

[56] References Cited

U.S. PATENT DOCUMENTS 4,337,529 6/1982 Morokana ............................ 368/10

Primary Examiner—Vit W. Miska
Attorney, Agent, or Firm—Birch, Stewart, Kolasch & Birch

[57] ABSTRACT

An apparatus for measuring the quantity of physical exercise in which the measurement of the quantity of physical exercise automatically ceases for intermissions of exercise, thereby providing an exact quantity of physical exercise.

9 Claims, 10 Drawing Figures

| FIG. 2A | FIG. 2B |

APPARATUS FOR MEASURING THE QUANTITY OF PHYSICAL EXERCISE

FIELD OF THE INVENTION

This invention relates to an apparatus for measuring the quantity of physical exercise in which apparatus the pace at which a person exercise (hereinafter referred to as "exercise pace") is determined from recurrent motions appearing in the body through the whole course of a physical exercise to calculate the quantity of motion on the basis of the "exercise pace" thus determined.

BACKGROUND OF THE INVENTION

Recently, exercises for keeping one's health have been polular, and among the aerobics, jogging has been favoured by many people as improving the functions of their hearts and lungs. The bodily exercises for the purpose of maintaining one's health, however, should be conducted in careful consideration of his age, the state of his health, the strength of his body, etc. Excessive quantity of exercise would injure his health. Sometimes, excessive exercise would cause one to take much food after finishing the exercise and hence he would become fat. Contrary to this, those who diet might suffer from anemia in the course of exercise. In this connection, the exact estimation of quantity of exercise is a matter of great concern.

In an attempt to meet this demand, a variety of exercise quantity measuring apparatuses have been hitherto proposed.

As is well known, the quantity of movement is represented by the product of a strength of movement and a time or period of movement. Some prior exercise gauges are designed to estimate the quantity of movement irrespective of intermittences or rests taken in the course of exercise, and therefore the estimation of the quantity of movement is not correct.

The exact estimation can be obtained by stopping the operation of the exercise gauge every time a person takes a rest in exercise and by starting the operation of the exercise gauge every time he resumes exercise. In case that an exercise continues a relatively long time with short intermissions now and then as for instance in jogging, however, the stopping-and-starting operations are too troublesome to repeat as many times as intermissions.

SUMMARY OF THE INVENTION

In an attempt to overcome the defects as mentioned above, this invention was made. Therefore, one object of this invention is to provide an apparatus for estimating the quantity of movement with accuracy without necessity of repeating the stopping-and-starting operation as many time as intermissions taken in exercise.

To attain this object, an apparatus for estimating the quantity of bodily exercise according to this invention is so constructed that: an "exercise pace" is determined from recurrent motions of parts of the body during a physical exercise; measurement of exercise time is made to cease in response to disappearance of recurrent motions in the body, which is regarded as a sign of the cease of exercise; measurement of exercise time resumes in response to the appearance of recurrent motions in the body, which is regarded as a sign of the resumption of exercise; and the quantity of exercise is calculated from the total of discrete lengthes of exercise time and the "exercise pace"; and the result of calculation is displayed.

BRIEF DESCRIPTION OF THE DRAWINGS

FIG. 2 which consists of FIGS. 2A and 2B is a block diagram of an apparatus for estimating the quantity of exercise according to one embodiment of this invention;

FIG. 5A shows a waveform representing the recurrent motions of a person who puts one foot down harder than the other foot in jogging whereas

DETAILED DESCRIPTION OF THE PREFERRED EMBODIMENTS

Before describing a sole embodiment of this invention with reference to the drawings, the method of calculating the quantity of exercise is described.

As mentioned earlier, the quantity of exercise is represented by the product of the strength of movement and the time or period of movement. The strength of movement in athletic sports, labours and other physical activities can be given as Relative Metabolic Rate as follows:

Relative Metabolic Rate =

$$\frac{\text{Metaboly in Exercise} - \text{Metaboly at Rest}}{\text{Basic Metaboly}}$$

Experimental data proves that the Relative Metabolic Rate in jogging is given by:

$$(CV-D)/E$$

where "V" stands for the average running speed; "C", "D" and "E" are constants given in the following table:

TABLE 1

|  | C | D | E |
|---|---|---|---|
| 50 ≦ V < 100 | 1 | 5 | 20 |
| 100 ≦ V < 140 | 1 | 0 | 20 |
| 140 ≦ V < 180 | 3 | 140 | 40 |
| 180 ≦ V < 240 | 1 | 80 | 10 |

In the book, "THE AEROBICS PROGRAM FOR TOTAL WELL BEING", written by Dr. K. H. Cooper, the author proposed a method of estimating the quantity of exercise. According to Dr. K. H. Cooper, the quantity of movement in jogging "$F_1$" can be calculated in terms of average running speed ($V_1$) and running distance ($L_1$) as follows:

TABLE 2

| $L_1$ | $V_1$ below 6 miles/hour | above 6 miles/hour |
|---|---|---|
| below 1 mile | $F_1 = (V_1 - 2) \times L_1$ | $F_1 = 2 \times V_1 \times L_{\frac{1}{2}}$ (1) |
| above 1 mile | $F_1 = (V_1 - 1) \times L_1 - 1$ | $F_1 (2 \times V_{\frac{1}{2}} + 1) \times L_1 - 1$ |

The average running speed $V_1$ (miles/hour) and the running distance $L_1$ (miles) are given by:

$$V_1 = \frac{0.0895 \cdot G \cdot L}{B} \text{; and}$$

$$L_1 = 0.0015 \times \frac{G \cdot L \cdot T}{D},$$

where "B" stands for running pace (seconds); "G" stands for pace-samping time; "L" stands for single stride in running (centimeters) and "T" stands for running time (minutes).

On the other hand, the quantity of movement in Kcal (kilocalorie) can be given by:

$$\text{quantity of movement (Kcal)} = RMR \times W \times A \times T \div 60 \qquad (2)$$

where "RMR" stands for Relative Metabolic Rate; "W" stands for the weight of a person (Kg); "A" stands for the coefficient of age adjustment (see Table 3) and "T" stands for the running time (minute).

TABLE 3

| Age | Coefficient of age adjustment (A) |
|---|---|
| 20 | 1.00 |
| 30 | 0.96 |
| 40 | 0.94 |
| 50 | 0.94 |
| 60 | 0.92 |
| 70 | 0.90 |

Now, a sole embodiment of this invention is described below with reference to drawings attached hereto.

Figure 1:
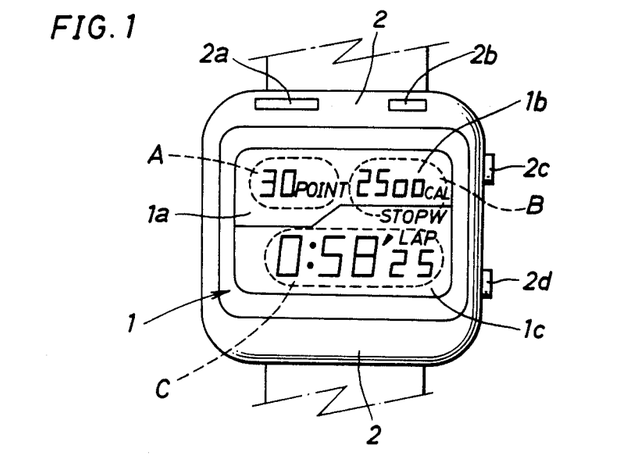
FIG. 1 shows a stopwatch equipped with an apparatus for estimating the quantity of exercise according to this invention.

FIG. 1 shows the face of a stopwatch equipped with an apparatus for measuring the quantity of movement according to the embodiment of this invention. As shown in FIG. 1, a display unit 1 has a display section 1a showing a quantity of exercise in terms of aerobics points as indicated at "A" (30 points); a display section 1b showing the same quantity of exercise in terms of calorie as indicated at "B" (2,500 calories); and a display section 1c showing time taken by exercise (0 hours 58 minutes 25 seconds). The stopwatch has four operation buttons, that is, a start/stop button 2a for stopping and starting the watch for measuring time taken by exercise; a lap/reset button 2b for indicating a lap time and for resetting the watch; a digit-changing button 2c; and a set button 2d. The digit-changing button 2c and the set button 2d can be used for putting individual data in an associated storage, too, as later described.

Figures 2, 2A:
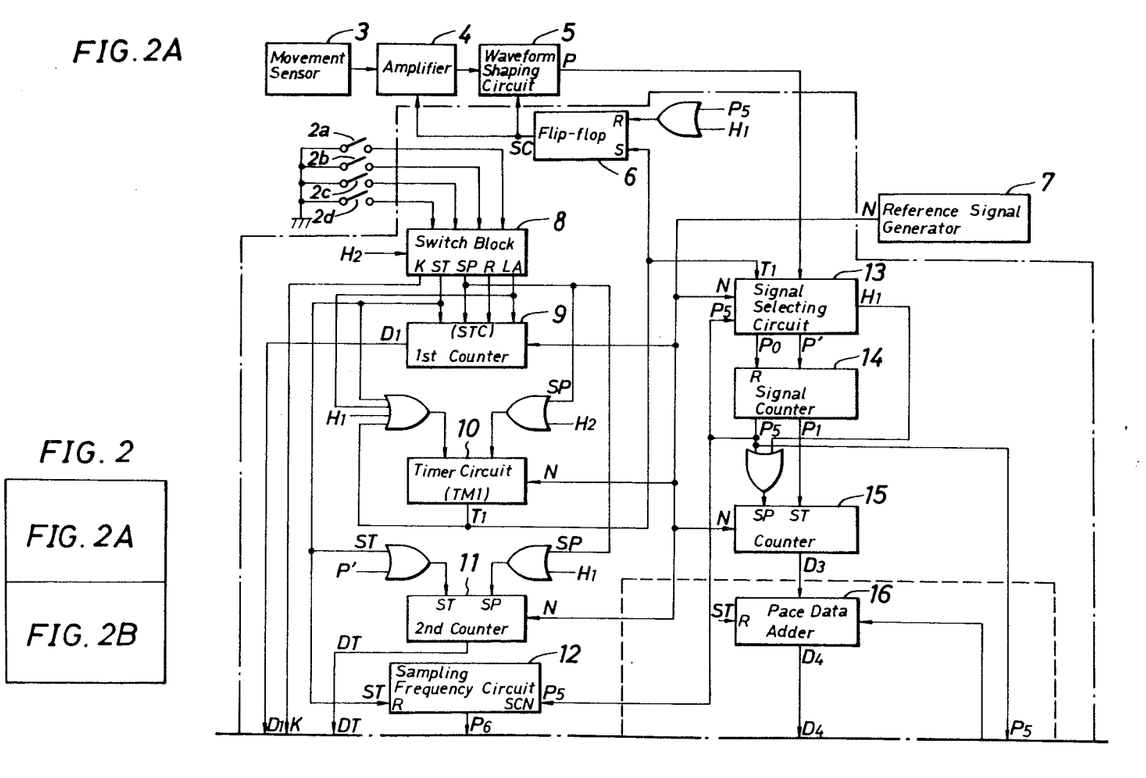
Figure 2B:
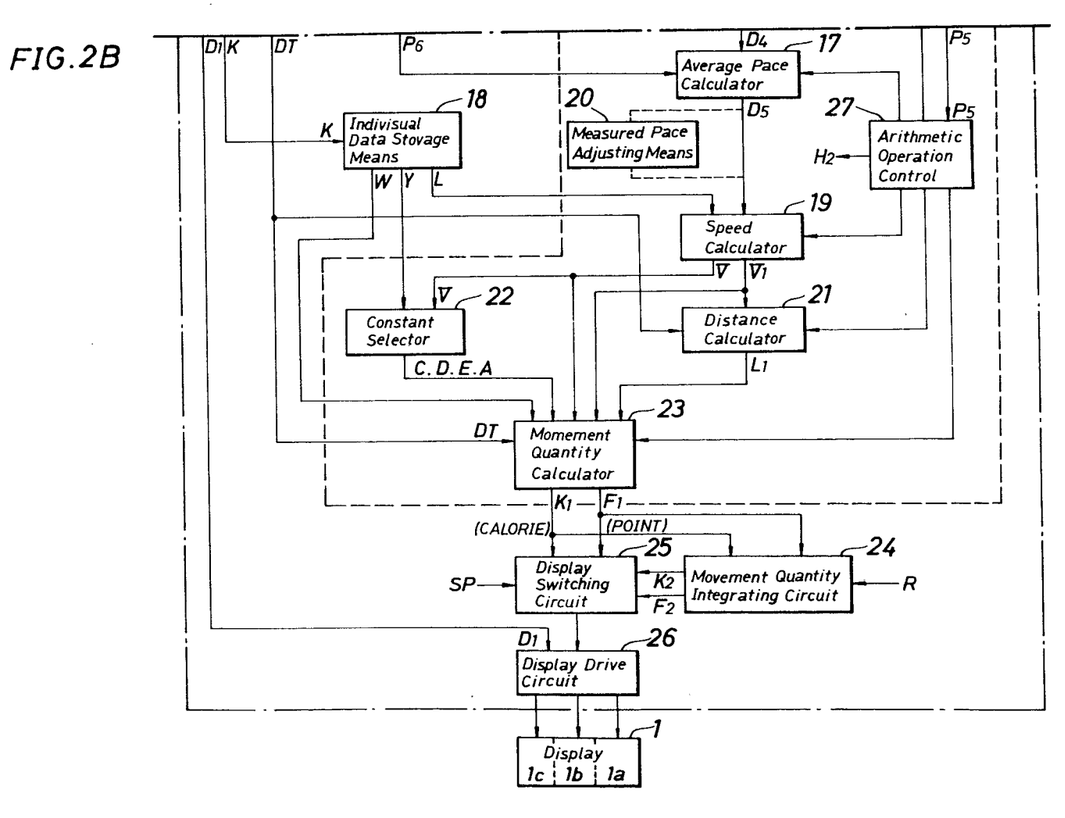

FIG. 2 shows a block diagram of an apparatus for measuring the quantity of movement in jogging according to the embodiment of this invention. A movement sensor 3 is used for transforming the number of arm swings in jogging to corresponding electric signals. A vibration detector using a piezoelectric element commercially available may be used for that purpose. Specifically, such a vibration detector comprises a metal weight and an associated piezoelectric element which is responsive to the magnitude of a force applied thereto for generating a voltage. The vibration detector is attached to the inside of the casing of the stopwatch. Thus, the piezoelectric element is subjected, through the agency of associated weight, to the force which is applied to the stopwatch when a runner swings his arms, and then the piezoelectric element generates a voltage at a level proportional to the magnitude of the force applied to the stopwatch.

The sensor 3 is connected to an amplifier 4 for selecting and amplifying electric signals in a given constant frequency range. The amplifier 4 is connected to a waveform shaping circuit 5 for shaping the output signals from the amplifier 4 into a train of pulses "P", which is referred to as "exercise signal". An R-S flip-flop 6 outputs pace-sampling signals SC when the flip-flop 6 is set by pulse signals $T_1$ as later described. The amplifier 4 and the waveform shaping circuit 5 are connected to the flip-flop 6, and the amplifier 4 and the shaper 5 are brought in their stand-by conditions when the pace-sampling signals SC are applied thereto. A reference signal generator 7 generates a reference signal N, for instance, at a frequency of 100 hertz. A switch block 8 is responsive to the closure of any of switches $SW_1$, $SW_2$, $SW_3$ and $SW_4$ associated with operating buttons 2a, 2b, 2c and 2d for outputting start signals ST for starting the measurement of time taken by exercise; stop signals SP for stopping the measurement of time, lap signals LA for presenting a lap time display; reset signals R for resetting a first counter 9; and individual data setting signals K for putting signal stride weight, age and other individual data.

A first counter (STC) 9 is responsive to the start signal ST for starting the measurement of time, and is responsive to the stop signal SP for stopping the measurement of time, thus determining the length of time $D_1$ elapsed from the start to the stop of measurement. Also, the first counter 9 is responsive to the lap signal LA for permitting the display of the lap time, and is responsive to reset signal R for resetting or vaporizing the count content.

A timer circuit (TM1) is responsive to the start signal ST or the lap signal LA for counting the reference signals N and for outputting pulse signal $T_1$ at regular intervals, for instance at intervals of two minutes. Thus, pace-sampling signals SC are provided at regular intervals on the basis of the pulse signals $T_1$, thereby sampling the exercise signal P to collect the pace data, as later described. This sampling operation is effective to save the electric power consumed in the amplifier 4.

A second counter (STM) 11 after resetting in response to the start signal ST, starts counting the reference signals N, and the second counter 11 stops counting in response to the stop signal SP or a motion-stop signal $H_1$, which is later described. Thus, the second counter 11 measures the length of time for which the exercise continues, outputting a signal representing an exercise time DT.

A sampling frequency counter (SCN) 12 counts measurement end signals $P_5$ from a signal counter 14 later described, thereby determining how many times the pace sampling was repeated, and outputting sampling frequency signals $P_6$. The sampling frequency counter 12 is reset in response to the start signal ST.

Figure 3:
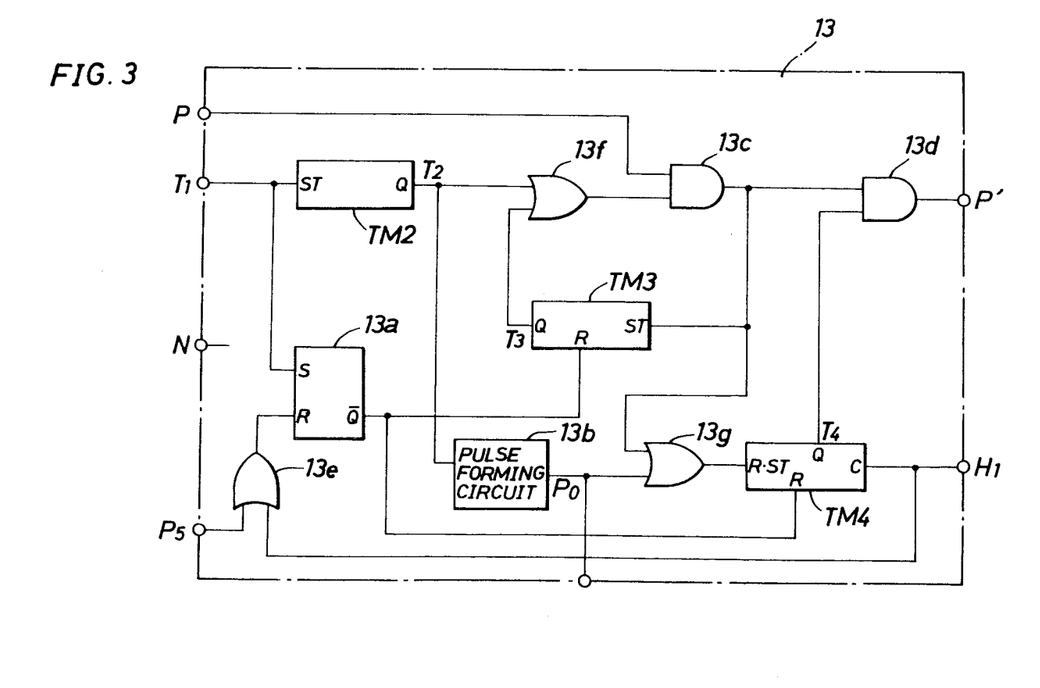
FIG. 3 is a wiring diagram of a signal selecting circuit appearing in FIG. 2.

A signal selecting circuit 13 makes a judging as to whether or not an interval between sequential exercise signals P supplied by the waveform shaping circuit 5 for the pace sampling period, that is, a running pace is within a predetermined range. Specifically, the signal selector 13 outputs signals P' corresponding to the exercise signals P when the interval between exercise signals or the running pace remains in the predetermined range, and the signal selector 13 outputs the exercise-stop signals $H_1$ when the interval between exercise signals is out of the predetermined range to indicate the intermission of jogging. FIG. 3 shows the signal selector 13 in details.

As shown in FIG. 3, the signal selector 13 is composed of three timer circuits TM2, TM3 and TM4, an R-S flip-flop circuit 13a, a pulse forming circuit 13b, two AND gates 13c and 13d and three OR gates 13e, 13f and 13g. The operation of the signal selector 13 is described later with reference to FIG. 4.

Referring back to FIG. 2, a signal counter 14 counts exercise signals P' supplied by the signal selector 13 for the pace-sampling period. The signal counter 14 is responsive to the first exercise signal P' for outputting the measurement start signal $P_1$, and is responsive to the fifth exercise signal P' for outputting the measurement end signal $P_5$. A counter 15 counts the reference signals N for a period of time from the measurement start signal $P_1$ to the measurement end signal $P_5$ supplied from the signal counter 14, thereby outputting a signal representing the running pace data $D_3$. The counter 15 is responsive to the measurement start signal $P_1$ for resetting and starting, and is responsive to the measurment end signal $P_5$ or the exercise end signal $H_1$ for stopping the counting operation.

A pace data adder 16 accumulates running pace data $D_3$ from the counter 15, thereby outputting accumulated pace data $D_4$. The adder 16 is responsive to the start signal ST for resetting.

An average pace calculator calculates an average jogging pace data $D_5$ from the accumulated pace data $D_4$ and the search frequency data $P_6$.

An individual data storage 18 is used for storing stride L, weight W, age Y and other individual data, which are supplied from the switch block 8. The storage device 18 is responsive to an individual data setting signal K for storing the individual data. The individual data setting signal K exists at one output terminal K of the switch block 8 by depressing the digit changing button 2c and the set button 2d together.

Figure 5A:
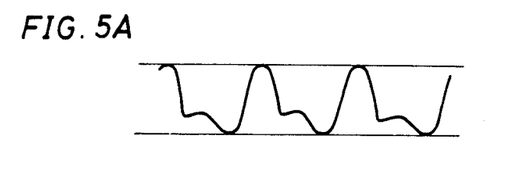
Figure 5B:
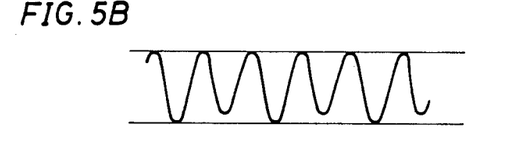
FIG. 5B shows a waveform representing the recurrent motions of a person who puts his feet down alternately with equal strength in jogging.

A jogging speed calculator 19 functions to multiply the average pace data $D_5$ from the average jogging pace calculator 17 for the stride data L from the individual data storage 18, thereby outputting an average jogging speed V (m/min.) or $V_1$ (mi/hr). In case that the average jogging pace data $D_5$ is below a given reference value (for instance, 100 m/min.), a measured pace adjusting means 20 doubles the average jogging pace data for the following reasons: some people put one foot down harder than the other foot in jogging whereas other people put the feet down with even strength in jogging. FIG. 5 shows the output signals from the amplifier 4 connected to the movement sensor 3 representing the abnormal rhythmical movement (FIG. 5A) and the normal rhythmical movement (FIG. 5A). As is apparent from these waveforms, the abnormal rhythmical movement is erroneously detected as one half of the frequency of the normal rhythmical movement. Therefore, the erroneous counting is corrected by doubling.

A jogging distance calculator 21 calculates a jogging distance $L_1$ from the average jogging speed $V_1$ and the exercise time DT from the second counter 11.

A constant selector 22 stores constants "C", "D" and "E" (Table 1), and age-adjusting coefficient "A" (Table 3), and selectively outputs constants and coefficients as required for calculating the quantity of movement from the average jogging speed $V_1$ and the age data "Y" from the individual data storage 18.

A device for calculating the quantity of movement 23 calculates first the quantity of movement $F_1$ according to an equation (1), which is selected from Table 2 in consideration of an average jogging speed $V_1$ and a jogging distance $L_1$, and second, the quantity of movement $K_1$ in terms of consumption calorie (Kcal).

A circuit for integrating the quantity of movement 24 integrates the quantity of movement $F_1$ and the consumption of calorie $K_1$ both calculated by the calculator means 23, thus outputting the integral of the quantity of movement $F_2$ and the integral of the consumption of calorie $K_2$.

A display switching circuit 25 allows the quantity of movement $F_1$ and the consumption calorie $K_1$ to pass therethrough during exercise. The display switching circuit, however, is responsive to the stop signal SP for preventing the quantity of movement $F_1$ and the consumption calorie $K_1$ from passing therethrough, but permitting the integral of the quantity of movement $F_2$ and the integral of the consumption of calorie $K_2$ to pass therethrough.

A display drive circuit 26 enables the elapsed time data $D_1$; the quantity of movement $F_1$ or the consumption calorie $K_1$; and the integral of the quantity of movement $F_2$ or the integral of the consumption calorie $K_2$ in the display sections 1a, 1b and 1c of the display 1, respectively.

An arithmetic operation control 27 performs timing control of the pace data adder circuit 16, the average jogging pace calculator 17, the jogging speed calculator 19, the jogging distance calculator 21 and the calculator for estimating the quantity of movement 23. The arithmetic operation control 27 is responsive to the measurement end signal $P_5$ for starting the timing control of an associated units, and outputting an operation inhibitng signal $H_2$. The application of the operation inhibiting signal $H_2$ to the switch block 8 disables the switch block 8 during the operation of these calculating units even if the buttons 2a to 2d are depressed.

The structure of the exercise gauge has been generally described above. Now, the signal selector circuit 13 which takes an important role in the operation of the exercise gauge, is described below in detail.

In FIG. 3, when a pulse signal $T_1$ from the timer circuit TM1 is applied to the start terminal ST of the timer circuit TM2, there exists a signal remaining at an "L" level for five seconds at the terminal Q of the timer circuit TM2. Assume that the reset terminal R of a timer circuit TM3 is kept at an "L" level, and that the start terminal ST thereof is brought to an "H" level, an "L" high signal $T_3$ exists at the terminal Q for 250 milliseconds. The "L" high signal $T_2$ appearing at the terminal Q of the timer circuit TM2 for 5 seconds is effective to eliminate the adverse effect by the noise which tends to appear in the amplifier 4 at the start of the operation of the amplifier, whereas the signal $T_3$ appearing at the terminal Q of the timer circuit TM3 for 250 milliseconds is effective to eliminate the adverse effect by the chattering noise which the exercise signal P tends to accompany.

Assume that the reset terminal R of the timer circuit TM4 is at the "L" level, and that the reset/start terminal R.ST thereof is brought to the "H" level. Then the timer circuit TM4 is reset instantaneously for starting, outputting an "H" high signal $T_4$ at the terminal Q of the timer TM4 for one second. Assume that the reset/start terminal R.ST is brought to the "H" level again. Then the timer TM4 is reset again for starting. If one second has passed without the occurrence of second starting, a carrier pulse $H_1$ exists at the carrier terminal of the timer TM4 at the end of the one second period. This carrier pulse signal $H_1$ is, in fact, an exercise end signal as described earlier.

The operation of the signal selector circuit 13 is described below with reference to FIG. 4.

As an initial condition in the signal selecting circuit 13 the terminal Q of the R-S flip-flop 13a for operation control is at the "H" level, and therefore the reset terminals R of the timer circuits TM3 and TM4 are at the "H" level, and are kept dormant. At that time, the output signal $T_2$ appearing at the output terminal Q of the timer circuit TM2 is at the "H" level. Thus, the AND gate 13c is ready to pass an exercise signal therethrough if applied, but the AND gate 13d is not ready to pass the exercise signal under the influence of the output signal from the timer circuit TM4, thus preventing the exercise signal P from passing through the signal selecting circuit and appearing as the signal P' at one output terminal of the signal selecting circuit.

(A) As for the period of time $t_1$ for which a person ceases exercise:

Assume that pace sampling pulse signals $T_1$ is applied to one input terminal of the signal selector 13 to set the R-S flip-flop 13a, thus reversing the potential at the terminal Q from the "H" level to the "L" level. Then, the reset terminals R of the timer circuits TM3 and TM4 are brought to the "L" level, thereby putting the timer circuits TM3 and TM4 in their stand-by conditions.

On the other hand, the timer circuit TM2 starts its operation in response to the pulse signal $T_1$, and the output signal $T_2$ remains at the "L" level for 5 seconds, thus preventing an exercise signal from passing through the AND gate 13c. After the lapse of five seconds the signal $T_2$ rises up to the "H" level to cause the pulse forming circuit 13b to output a signal selection starting signal $P_0$, thereby resetting the timer circuit TM4 instantaneously and immediately allowing the timer circuit TM4 to start its operation. At that time, the timer circuits TM2 and TM4 put the AND gates 13c and 13d in condition for passing exercise signals P therethrough. No exercise signals P, however, appear because the jogging ceases.

If one second has passed in this situation, the operation of the timer circuit TM4 ends and the exercise end signal $H_1$ exists at the carrier terminal C of the timer circuit TM4 simultaneously with the closure of the AND gate 13d. The exercise end signal $H_1$ is applied to the R-S flip-flop 13a through the agency of the OR gate 13e for resetting the R-S flip-flop, and then the signal selecting circuit 13 returns to its dormant state. Thus, one signal selection ends.

(B) As for a relatively short period of time $t_2$ for which the person exercise:

Assume that he exercises for a relatively short period of time, for instance, one minute, and that the movement sensor 3 detects the swinging of his arms, thus causing a single exercise signal P to appear. As is the case with the event (A), when the pulse signal $T_1$ from the timer circuit 10 is applied to the timer circuit TM2 in the signal selecting circuit 13, the potential at the output terminal $T_2$ of the timer circuit TM2 is kept at the "L" level for five seconds. If a signal selection starting signal $P_0$ exists at the output terminal of the pulse forming circuit 13b at the lapse of the period of five seconds, an "H" high signal exists at the Q terminal of the timer circuit TM4 for one second. After five seconds have lapsed subsequent to the arrival of the pulse signal $T_1$ at the signal selecting circuit 13, and while the Q terminal of the timer circuit TM4 remains at the "H" level, an exercise signal P is allowed to pass through the AND gates 13c and 13d, thereby appearing at one output terminal of the signal selecting circuit as the signal P'. The exercise signal P after passing through the AND gate 13c is directed to the timer circuit TM4 via the OR gate 13g. Thus, the timer circuit TM4 is reset and immediately started, thereby causing an "H" high signal $T_4$ to appear at the Q terminal of the timer circuit TM4 for one second.

On the other hand, after passing through the AND gate 13c the exercise signal P is directed to the start terminal ST of the timer circuit TM3 to cause the timer circuit TM3 to output a 250 millisecond long and "L" high signal $T_3$. No exercise signals P follow, and therefore at the Q terminal of the timer circuit TM4 there exists an "L" high signal after the lapse of one second subsequent to the arrival of the above mentioned exercise signal P whereas at the carrier terminal C of the timer circuit TM4 there exists an exercise end signal $H_1$, thus indicating the intermission or end of the exercise. Thanks to the appearance of the exercise end signal H, the R-S flip-flop 13a is reset, thereby causing the potential at the Q terminal to rise to the "H" level. As a result, the timer circuits TM3 and TM4 are reset, and then the operation of the signal selecting circuit 13 ends.

As seen from the above, in case that the exercise continues so short a period of time that only one exercise signal P exists at the output terminal of the waveform shaping circuit, the exercise pace cannot be detected. Then, it is decided that no exercise is taken.

(C) As for a period of time $t_3$ for which the exercise continues:

In this case the exercise sensor 3 outputs a train of exercise signals P at regular intervals.

Assume that the pulse signal $T_1$ is applied to the timer circuit TM2 and that a five-second dormant time has passed. Then, the pulse forming circuit 13b outputs a signal-selection starting signal $P_0$. After being reset by the signal-selection starting signal $P_0$, the timer circuit TM4 starts and outputs an "H" high signal $T_4$ at the Q terminal of the timer circuit TM4 for one second. If the first exercise signal P arrives within the one second, the AND gates 13c and 13d allow the first exercise signal to pass therethrough, and then the signal P' exists at the output terminal of the AND gate 13d. On the other hand, after passing through the AND gate 13c the exercise signal P is directed to the timer circuits TM3 and TM4, thus causing the timer circuit TM3 to output and "L" high signal $T_3$ for 250 milliseconds.

Assume that the second exercise signal P arrives within one second subsequent to the arrival of the first exercise signal and after the lapse of the dormant time of 250 milliseconds. Then, the AND gates 13c and 13d allow the second exercise signal to pass therethrough, and then an output signal P' exists at the output terminal of the AND gate 13d. The timer circuits TM3 and TM4 operate in the same way as in the case of the first exercise signal P. Specifically, the timer circuit TM3 outputs a 250 millisecond long and "L" high signal $T_3$ whereas the timer circuit TM4 after being reset, starts and outputs a one second long and "H" high signal $T_4$. Thereafter the third exercise signal P arrives within one second, and then the fourth exercise signal P arrives within one second in sequence. Then timer circuits TM3 and TM4 operate in the same way, and the signal P' exists one after another.

Assume that the fifth exercise signal P arrives within one second subsequent to the arrival of the fourth exercise signal, and then as a matter of course, a signal P' exists. when the signal counter 14 which follows the signal selecting circuit counts the fifth signal, a measurement end signal $P_5$ exists at the output terminal of the signal counter 14. When the measurement end signal $P_5$ is fed back to the signal selecting circuit 13, the flip-flop 13a is reset, thereby causing an "H" high signal to exist at the Q terminal of the flip-flop 13a. As a consequence the timer circuits TM3 and TM4 are reset, and then the operation of the signal selecting circuit 13 ends.

Figure 4:
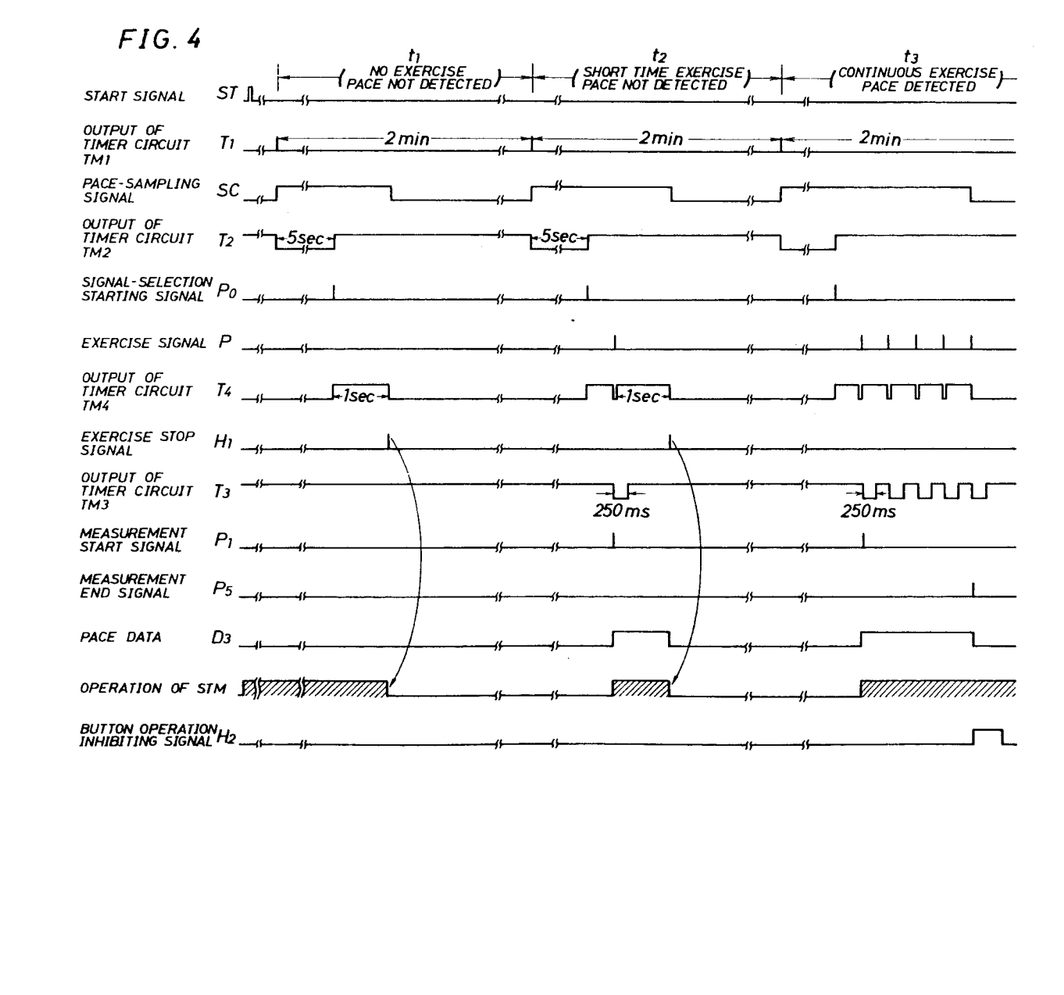
FIG. 4 is a timing chart showing different waveforms appearing in some elements of the signal selecting circuits and other electrical circuits in the exercise gauge.

As is apparent from the timing chart of FIG. 4, when the signal selecting circuit 13 outputs an exercise end signal $H_1$, the operation of the second counter (STM)11 stops. The second counter (STM)11 starts its operation in response to a start signal or an exercise signal P (or P'), and it stops its operation in response to a stop signal SP or an exercise end signal $H_1$. Thus, the counting operation continues exclusively through the whole period of time for which the exercise or jogging continues. Therefore, the exact period of time taken by the exercise or jogging DT is measured (see the hatchings in FIG. 4).

The amplifier 4, the waveform shaping circuit 5, the reference signal generator 7, a one-chip microprocessor for performing arithmetic operations and controls as required, and a storage (enclosed with broken lines in FIG. 2) are integrated together in an integrated circuit. Then the integrated circuit and the movement sensor 3 are built in a stopwatch, and the display unit 1 is provided in sight.

Figure 6A:
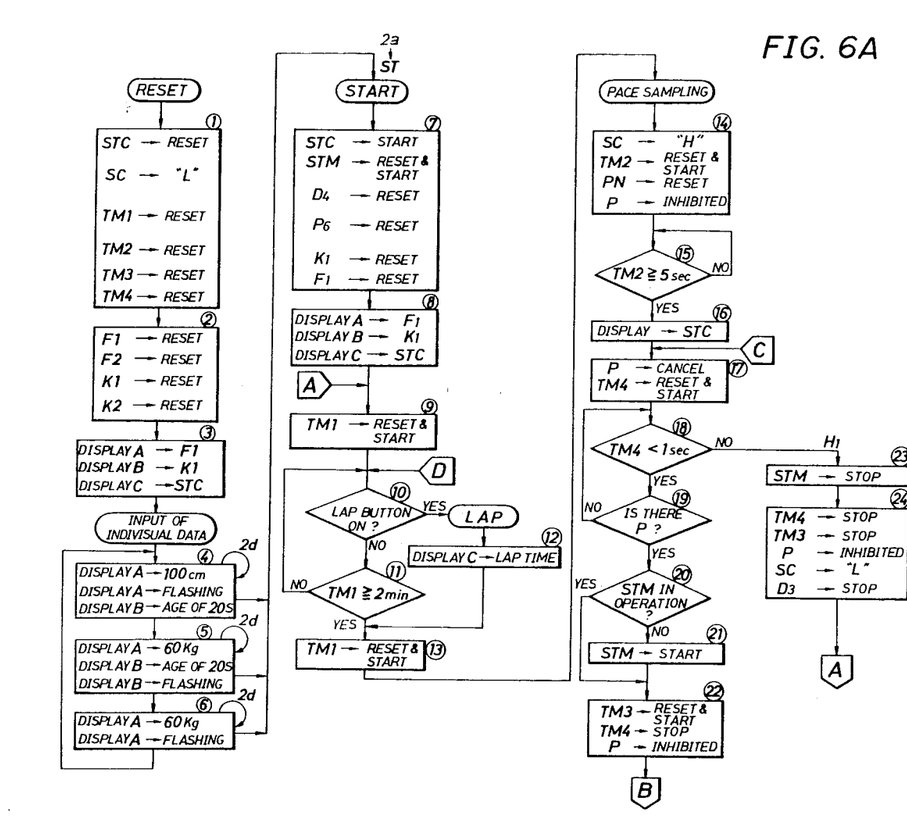
FIGS. 6A and 6B in combination shows a flow chart showing the proceedings conducted in the exercise gauge according to this invention.
Figure 6B:
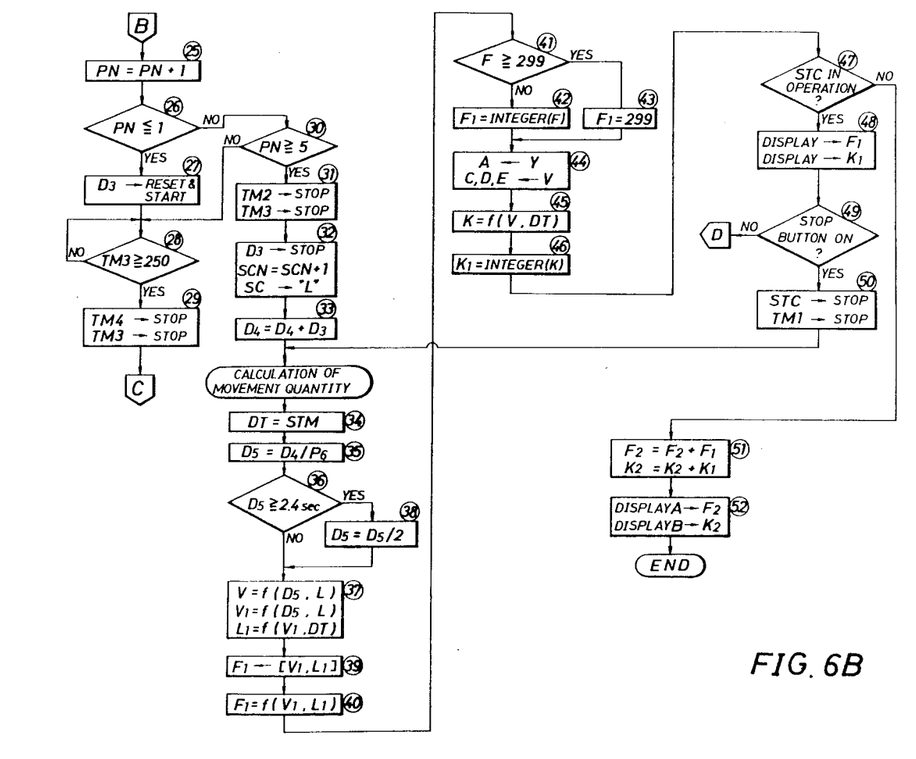

The arithmetic operation for estimating the quantity of exercise is performed by a microprocessor according to a predetermined program, which is described later with reference to the flow chart of FIGS. 6A and 6B. Only for the sake of convenience, a general description of a stopwatch equipped with an exercise gauge according to this invention is given just below.

It is necessary to store individual data prior to the start of the measurement of the quantity of exercise. The depression of the operation buttons 2a to 2d causes the switch block 8 to output an individual data storage signal k, thereby storing the stride L, weight W and age Y of a runner in the storage 18. The runner depresses the start/stop button 2a simultaneously with the start of jogging, and then a start signal ST is generated and is directed to the first counter 9, thus beginning the counting of the reference signals N. At the same time, the start signal ST is directed to the second counter 11, thereby resetting the second counter 11, and immediately thereafter starting the counting of the reference signals N. In this condition the first counter 9 supplies the display drive circuit with elapsed time data $D_1$, thus presenting the time elapsed in the display section 1c of the display unit 1. The movement sensor 3 outputs signals synchronously with the swinging of the runner's arms while the first counter 9 is in operation. Simultaneously with the beginning of the counting of the reference signals N in the first counter 9, the timer circuit 10 starts the counting of the reference signals N, and the timer circuit 10 outputs pulse signals $T_1$ at regular intervals (for instance, at intervals of two minutes). The amplifier circuit 4 and the waveform shaping circuit 5 are on stand-by in response to the pulse signals $T_1$ from the timer circuit 10. Thus, the pace sampling is conducted at regular intervals, thereby saving the electric power which otherwise would be consumed by the amplifier circuit 4. The pulse signals $T_1$ are directed to the signal selecting circuit 13 for indicating the start of every pace sampling. The operation of the signal selecting circuit 13 is described above in detail with reference to FIGS. 3 and 4, and is summarized below.

After a predetermined period of time (for instance, 5 seconds) has passed subsequent to the arrival of the pulse signal $T_1$ at the signal selecting circuit 13, the pulse forming circuit 13b in the signal selecting circuit 13 outputs a signal selection starting signal $P_0$, and thereafter exercise signals P originating from the movement sensor 3 may be accepted and processed in the signal selecting circuit as follows: assume that the first exercise signal P arrives at the signal selecting circuit 13 within one second subsequent to the time at which the signal selecting circuit 13 is ready to accept exercise signals, and that the second exercise signal P arrives in 250 or more milliseconds (predetermined minimum time) but within one second (predetermined maximum time) subsequent to the appearance of the first exercise signal. Then, the second exercise signal P can pass through the signal selecting circuit 13 to exist at one output terminal of the signal selecting circuit. Likewise, subsequent exercise signals P are outputted, provided that the interval between adjacent exercise pulses is above 250 or more milliseconds, but below one second. An exercise stop signal $H_1$ is outputted if no exercise signal arrives at the signal selecting circuit 13 after the lapse of the predetermined maximum time. The second counter 11 is responsive to the exercise stop signal $H_1$ for stopping its counting action and the counter 15 stops its counting action, too.

Specifically when the exercise taken by the person is less active or when the person takes an intermission without stopping his stopwatch, the second counter 11 stops its counting operation. The timer circuit 10 outputs pulse signals $T_1$ at regular intervals of, for instance, two minutes synchronously with the start signals ST from the switch block 8. However, if the switch block 8 outputs lap signals LA, the timer circuit 10 outputs pulse signals $T_1$ synchronously with the lap signals, and at the same time, the timer circuit 10 is reset and then it immediately starts. Thus, the pulse signals $T_1$ from the timer circuit 10 are outputted synchronously with the start signals ST in every two minutes, and synchronously with the lap signals LA and in every two minutes. Assume that the second counter 11 intermits its counting in response to the exercise end signal $H_1$, and then pace sampling is conducted in response to the subsequent pulse signal $T_1$, and if an exercise signal P arrives within a predetermined time, the signal selecting circuit 13 releases an exercise end signal $H_1$, thereby resuming the measurement by the second counter 11. The exercise signal P after passing through the signal selecting circuit 13 is directed to the signal counter 14. The signal counter 14 is responsive to the first exercise signal P' for outputting a measurement start signal $P_1$, and is responsive to the fifth exercise signal P' for outputting a measurement end signal $P_5$. On the other hand, the sampling frequency counter 12 is responsive to the start signal ST for resetting, and then it counts the measurement end signals $P_5$, thereby providing the sampling frequency $P_6$. The counter 15 measures the time interval between the measurement start signal $P_1$ and the measurement end signal $P_5$ to output a signal representing a runner's jogging pace $D_3$. The jogging pace signal $D_3$ is directed to the pace data adder 16, which stores pace data added one after another. The average pace calculater 17 determines an average pace $D_5$ per minute from pace summation data $D_4$ supplied by the pace data adder 16 and the sampling frequency data $P_6$ supplied by the sampling frequency counter 12. The calculated result is checked by the measured pace adjusting means 20, and if the average pace $D_5$ is below 100, the result of calculation is doubled. The average pace data $D_5$ is multiplied by the stride L of the runner to provide the average jogging speed T or $V_1$, and then the running distance $L_1$ is determined from the average jogging speed V or $V_1$ and the exercise timer DT from the second counter 11.

Next, the arithmetic unit 23 for calculating the quantity of movement estimates $F_1$ according to an appropriate equation (1) which is selected from Table 2 in consideration of the average speed $V_1$ and the jogging distance $L_1$, and at the same time, the calculator 23 estimates the consumption calorie $K_1$ according to the equation (2) with his weight and an age adjustment coefficient substituted for "W" and "A". The arithmetic operation control 27 outputs an inhibiting signal $H_2$ to inhibit the operation of the switch block 8 through the whole period of the estimation of the quantity of movement $F_1$ and the consumed calorie $K_1$. The quantity of movement $F_1$ and the consumed calorie $K_1$ are presented in the display sections 1a and 1b of the display unit 1 through the agency of the display drive 26.

The operation of measurement of the quantity of movement according to this invention is described below with reference to the flow chart of FIG. 6. Hereinafter the first counter 9 for measuring the time elapsed is referred to as STC; the timer circuit 10 for setting the interval between subsequent pace sampling (interval of two minutes) is referred to as TM1; the second counter 11 for measuring a period of time for which an exercise continues is referred to as STM; and pace sampling frequency counter 11 is referred to as SCN. At the first stage the lap/reset button 2b is depressed to reset the stopwatch, specifically reset the first counter STC, the timer circuit TM1, and the timer circuits TM2, TM3 and TM4 which together constitute the signal selecting circuit 13. At the same time, an "L" high pace sampling signal SC is applied to the amplifier circuit 4, thereby putting the same in condition ready for operation.

At the second stage, the quantity of movement $F_1$, the integral of the quantity of movement with respect to time $F_2$, the consumed calorie $K_1$ and the integral of the consumed calorie with respect to time are reset. At the third stage, the display data in each display section 9 of the display unit 1 are renewed: display A in the display section 1a is allotted to the quantity of movement $F_1$; display B in the display section 1b to the consumed calorie $K_1$; and display C in the display section 1c to the content of the first counter STC.

At the fourth, fifth and sixth stages necessary individual data are set right. Depression of the selection button 2c puts the exercise gauge in condition for accepting individual data.

Specifically at the fourth stage the stride of a person is set. First, the standard stride of 100 cm is flash-displayed in the display section 1a and the period of his life (between the ages of 20 and 29) is displayed in the display section 1b in which his age to be set is displayed. In this condition, depression of the operation button 2d is repeated to reduce or increase the stride little by little in the display section 1a until his stride L existss therein.

At the fifth stage, his age is set. Depression of th digit-changing button is repeated to flash the period of his life (between the ages of 20 and 29), and the standard weight (of 60 kg) is displayed in the display section 1a in which his weight to be subsequently set is displayed. In this condition depression of the operation button 2d is repeated to change the figure in the display section 1b to his age, thus setting his age Y.

At the sixth stage, his weight is set. Depression of the digit-changing button 2c flashes the standard weight of 60 kg in the display section 1a, and in this condition depression of the set button 2d is repeated to change the figure little by little in the display section 1a to his weight W, thus setting his weight W.

Then, simultaneously with the start of exercise the start/stop button 2a is depressed, to start the measurement of the quantity of movement. At that time the switch block 8 outputs a start signal ST.

At the seventh stage, the first counter STC starts, and at the same time, the second counter STM is reset and immediately starts. Also, the pace addition data $D_4$ from the pace data adder 16, the sampling frequency data $P_6$ from the sampling frequency counter 12 and the consumed calorie $K_1$ and the quantity of movement $F_1$ are reset.

At the eighth stage $F_1$ (display A) is presented in the display section 1a; $K_1$ (display B) is presented in the display section 1b and the count of the first counter STC (display C) is presented in the display section 1c. At the ninth stage, the timer circuit TM1 is reset, and immediately it starts.

At the tenth stage, a judging is made is to whether the lap operation has been performed or not. In the affirmative case the lap time is presented in the display section 1c at the twelfth stage whereas in the negative case a judging is made as to whether the elapsed time is above two minutes or not. If the elapsed time is above two minutes, an advance is made to the thirteenth stage at which the timer circuit TM1 is reset, and it immediately starts. Otherwise, if the elapsed time is below two minutes, the tenth and eleventh stages are circulated until two minutes have elapsed.

Now, the pace sampling starts.

At the fourteenth stage, the flip-flop 6 is set by the pulse signals $T_1$ which are supplied by the timer circuit TM1 at intervals of two minutes, thereby outputting pace sampling signals SC. At the same time, the timer circuit TM2 in the signal selecting circuit 13 is reset, and then the timer circuit starts immediately. The signal selecting circuit 13 is inhibited from receiving exercise signals P for the period of five seconds for which the timer circuit TM2 remains dormant, and thereafter the signal counter 14 is reset for preparation for the subsequent counting in response to a signal selection starting signal $P_0$, which is supplied by the signal selecting circuit 13.

At the fifteenth stage a judging is made as to whether five seconds for which the timer circuit remains dormant have elapsed or not. In the affirmative case the measurement data of the first counter STC is presented in the display section 1c at the sixteenth stage. If the lap time is displayed in the display section 1c, the lap time display is automatically vapourized, and the count result of the first counter STC is presented as a substitute.

At the seventeenth stage, the inhibition of acceptance of exercise signals P is removed, and the timer circuit TM4 is reset by a signal selection starting signal $P_0$, and the timer circuit TM4 starts.

At the eighteenth and ninteenth stages, a judging is made as to whether an exercise signal P arrives before the lapse of one second for which the timer circuit TM4 remains dormant or not. In the affirmative case an advance is made to the twenty-third stage, at which the second counter STM for measuring the period of time for which the exercise continues, is made to stop by an exercise stop signal $H_1$ which is supplied by the timer circuit TM4 after the lapse of one second.

At the twenty-fourth stage, the timer circuits TM4 and TM3 are reset, thereby inhibiting the acceptance of exercise signals P, and at the same time the flip-flop 6 is reset, thereby causing the pace sampling signal SC to turn to the "L" level. Thus, the pace sampling ends, and the proceeding returns to the ninth stage.

At the ninteenth stage, an exercise signal P is received, and then at the twentieth stage a judging is made as to whether the second counter STM is then in operation or not. Stated otherwise, a judging is made as to whether the second counter STM stops as a result of absence of exercise signals in the previous pace sampling (no exercise taken). If the second counter STM, in fact, stops, it is made to start at the twenty-first stage.

At the twenty-second stage, the timer circuit TM3 of the signal selecting circuit 13 is reset, and immediately, it starts. On the other hand, the timer circuit TM4 is made to stop, and exercise signals are inhibited.

At the twenty-fifth stage the signal counter 14 counts the number PN of the exercise signals P. At the twenty-sixth stage, a judging is made as to whether the number PN is one or more than one. If the number PN is equal to one, the counter 15 is reset, and then it immediately starts.

At the twenty-eighth stage, a judging is made as to whether the dormant period of time (250 milliseconds) of the timer circuit TM3 has passed or not, and if the dormant period of time has elapsed, the timer circuits TM3 and TM4 are made to stop at the twenty-ninth stage, and the proceeding returns to the seventeenth stage. Thus, exercise signals P are accepted after the lapse of 250 milliseconds for the timer circuit TM3 and before the lapse of one second for the timer circuit TM4.

The actions from the seventeenth to twenty-ninth stages are repeated with each of four exercise signals. The actions proceed from the twenty-sixth to twenty-eighth stage, bypassing the twenty-seventh stage.

The count number PN of the exercise signals counted by the signal counter 14 is equal to five at the time of arrival of the fifth exercise signal P. Then, an advance is made to the thirty-first stage, and the timer circuits TM3 and TM4 stop.

At the thirty-second stage the counter 15 stops, and the R-S flip-flop 6 is reset, turning the pace sampling signal SC to the "L" level. The sampling frequency counter SCN increases the counter content by one.

At the thirty-third stage, the pace data adder 16 provides a summation of pace data $D_3$ supplied so far (i.e., pace total data $D_4$). At the thirty-fourth and subsequent stages the quantity of movement is calculated.

At the thirty-fourth stage, the count in the second counter STM represents exercise time data DT.

At the thirty-fifth stage the average pace counter 17 estimates an average pace data $D_5$ by deviding the pace total data $D_4$ from the pace data adder 16 by the pace sampling frequency data $P_6$ from the pace sampling frequency counter SCN.

At the thirty-sixth stage, a judging is made as to whether the average pace thus determined is above a given reference or not. Specifically, if the average pace is above 2.4 seconds, the measured pace adjusting means 20 adjusts the average pace data by halving the average pace for the following reasons: if the average pace is below 100 strides per minutes, the runner is regarded as swinging his arms once for every two strides, and necessary adjustment is made by doubling the average pace.

At the thirty-seventh stage, the jogging speed calculator 19 determines an average jogging speed $V_1$ or V from the average pace data $D_5$ and the stride data L whereas the jogging distance calculator 21 determines an average jogging distance $L_1$ from the average jogging speed $V_1$ and the exercise time DT.

At the thirty-ninth stage, one equation is selected out of the four equations given in Table 2 in consideration of the average jogging speed $V_1$ and the average jogging distance $L_1$ both determined at the thirty-eighth stage, and at the fortieth stage, the arithmetic unit 23 determines the quantity of exercise.

The forty-first stage is provided because of the display limitations in display unit of the stopwatch, and at this stage a judging is made as to whether the quantity of exercise $F_1$ is above 299 or not. In the affirmative case the quantity of exercise is displayed as equal to 299 (at the forty-third stage) whereas in the negative case the quantity of exercise is displayed in terms of a closest integral number (at the forty-third stage).

At the forty-fourth stage the constant selector 22 selects an appropriate age adjustment coefficient A from Table 3 in consideration of the age data Y stored in the storage 18, and selects constants C, D and E from Table 1 in consideration of the average running speed V which is determined by the speed calculator 19.

At the forty-fifth stage, the Relative Metabolic Rate is determined from the constants C, D and E and the average running speed V where as the consumed calorie $K_1$ is determined from the equation (2) on the basis of the weight W, the age adjustment coefficient A and the exercise time DT. At the forty-sixth stage the consumed calorie $K_1$ is changed to a closest integral number K so as to be in conformity with the capability of the display unit. At the forty-seventh stage, a judging is made as to whether the second counter STC is now in operation or not. In the affirmative case, at the subsequent stage, the quantity of exercise $F_1$ in terms of point and the consumed calorie $K_1$ are presented in the display sections 1a and 1b respectively.

At the forty-ninth stage a judging is made as to the start/stop button 2a is depressed or not, and in the negative case the proceeding returns to the tenth stage. In the affirmative case a stop signal ST exists and then at the subsequent fiftieth stage the first counter STC and the timer circuit TM1 stop. Then, the proceeding returns to the thirty-fourth stage, and the proceeding goes through the thirty-fourth to forty-sixth stages, and from the forty-seventh stage to the fifty-first stage.

At the fifty-first stage the circuit 24 for integrating the quantity of movement with respect to time integrates the quantity of movement $F_1$ and the consumed calorie $K_1$ with respect to time, thereby determining the integral of the quantity of movement $F_2$ and the integral of the quantity of consumed calorie $K_2$.

At the fifty-second stage the display switching circuit 25 switches displays A and B to the integral of the quantity of movement F and the integral of the quantity of consumed calorie $K_2$ in the display sections 1a and 1b respectively.

The embodiment is described as being applied to a stopwatch. As a matter of course an apparatus for measuring the quantity of physical exercise according to this invention may be used as a separate and independent unit.

The exercise gauge according to the embodiment of this invention is described as estimating the quantity of movement in jogging. It, however, should be understood that the exercise gauge may be used for measuring the quantity of movement in swimming, ropeskipping, etc., simply by using arithmetic equations appropriate for a particular exercise.

As is apparent from the above, in the operation of an exercise gauge according to this invention, an exercise pace is detected on the basis of the movement of one's body in exercise; the measurement of time taken by exercise is made to stop when no exercise pace can be detected (this situation being regarded as a sign of intermission of exercise); the measurement is made to resume in response to the resumption of exercise; and the quantity of movement is calculated from the exercise pace and the time taken by exercise. Thus, the quantity of movement can be determined on the basis of the real length of time taken by exercise and including no intermissions, thereby providing the exact measurement of the quantity of exercise. Exercise paces are detected at regular intervals, thereby permitting the saving of electric power to the extent that an exercise gauge according to this invention may be built in a stopwatch or wristwatch.

From the angle of human engineering, the exercise pace is adjusted to compensate for individual variations in jogging, thereby permitting the calculation of the quantity of movement with accuracy.

The quantity of movement is displayed in terms of aerobics point or calorie, thereby facilitating the judging as to whether the quantity of movement is appropriate for the age, strength of body and health of a person taken the exercise.

What is claimed is:

1. An apparatus for measuring the quantity of physical exercise comprising:

exercise time measuring means for measuring a length of time for which the physical exercise continues;

movement detecting means responsive to movement of the body of a person taking the exercise for generating movement signals each representing the movement of the body;

exercise pace detecting means for measuring intervals between subsequent movement signals and detecting an exercise pace;

individual data storage means for storing at least the stride of the person;

judging means for making a judging as to whether movement signals exist or not;

arithmetic means for calculating the quantity of movement on the basis of the exercise time, the stride and the exercise pace; and display means for displaying the quantity of movement thus calculated, whereby the time measurement by said exercise time measuring means is controlled on the basis of the judgment made by said judging means.

2. An apparatus for measuring the quantity of physical exercise according to claim 1 wherein if further comprises sampling means for generating sampling signals at regular intervals, thereby permitting said judging means to make a judgment as to whether movement signals exist or not at regular intervals.

3. An apparatus for measuring the quantity of physical exercise according to claim 1 wherein said individual data storage means further includes means for storing data of one's weight and data of one's age.

4. An apparatus for measuring the quantity of physical exercise according to claim 1 wherein said arithmetic means is capable of calculating the quantity of physical exercise in calorie by multiplying the quantity of physical exercise by data of weight and data of age as adjustment coefficients.

5. An apparatus for measuring the quantity of physical exercise according to claim 1 wherein it further comprises pace judging means for making a judging as to whether said exercise pace is below a given reference value or not, and measured pace adjustment means for doubling the measured pace if the measured pace is below said given reference value.

6. An apparatus for measuring the quantity of physical exercise according to claim 1 wherein it further comprises arithmetic means for expressing the quantity of exercise in the range of aerobics in terms of point.

7. An apparatus for measuring the quantity of physical exercise according to claim 4 further comprises integrating means for integrating the quantity of exercise with respect to time.

8. An apparatus for measuring the quantity of physical exercise according to claim 2 wherein said sampling means if capable of generating sampling signals at intervals of two minutes.

9. An apparatus for measuring the quantity of physical exercise according to claim 6 wherein it further comprises integrating means for integrating the quantity of exercise with respect to time.

* * * * *

UNITED STATES PATENT AND TRADEMARK OFFICE
CERTIFICATE OF CORRECTION

PATENT NO. : 4,525,074
DATED : June 25, 1985
INVENTOR(S) : Tomomi MURAKAMI

It is certified that error appears in the above-identified patent and that said Letters Patent is hereby corrected as shown below:

IN THE HEADING OF THE PATENT

Add section [30] to read:

--Aug. 19, 1983 [JP] Japan.........151091/83--
--Nov. 8, 1983 [JP] Japan..........209551/83--
--July 27, 1984 [JP] Japan.........155420/84--

Signed and Sealed this

Twenty-fourth Day of September 1985

[SEAL]

Attest:

Attesting Officer

DONALD J. QUIGG

Commissioner of Patents and
Trademarks—Designate